United States Patent
Mikkonen et al.

(10) Patent No.: US 6,441,206 B1
(45) Date of Patent: Aug. 27, 2002

(54) USE OF ORGANIC ACID ESTERS IN DIETARY FAT

(75) Inventors: Hannu Mikkonen, Rajamäki; Elina Heikkilä, Vantaa; Erkki Anttila, Rajamäki; Anneli Lindeman, Espoo, all of (FI)

(73) Assignee: Raisio Benecol Ltd., Raisio (FI)

( * ) Notice: Subject to any disclaimer, the term of this patent is extended or adjusted under 35 U.S.C. 154(b) by 0 days.

(21) Appl. No.: 09/508,295

(22) PCT Filed: Sep. 9, 1998

(86) PCT No.: PCT/FI98/00707

§ 371 (c)(1),
(2), (4) Date: May 12, 2000

(87) PCT Pub. No.: WO99/15546

PCT Pub. Date: Apr. 1, 1999

(30) Foreign Application Priority Data

| Sep. 9, 1997 | (FI) | 973647 |
| Dec. 18, 1997 | (FI) | 974563 |
| Dec. 30, 1997 | (FI) | 974648 |

(51) Int. Cl.[7] ................................. C07J 9/00
(52) U.S. Cl. ........................ 552/540; 554/213
(58) Field of Search ................ 554/213; 882/540

(56) References Cited

U.S. PATENT DOCUMENTS

| 4,304,726 A | 12/1981 | Arakawa et al. |
| 5,502,045 A | 3/1996 | Miettinen et al. |

FOREIGN PATENT DOCUMENTS

| CH | A5681891 | 6/1993 |
| DE | 2113215 C2 | 10/1971 |
| DE | 19701264 A1 | 7/1998 |
| EP | A2430078 | 5/1991 |
| EP | 430078 | * 6/1991 |
| GB | 938937 | 10/1963 |
| GB | 1298047 | 11/1972 |
| GB | 2288805 | * 7/1995 |
| JP | 588098 A | 1/1983 |
| JP | 9194345 A | 7/1997 |
| JP | A1114790 | 5/1998 |
| SE | 574450 | 9/1993 |
| WO | A19806405 | 2/1998 |

OTHER PUBLICATIONS

Miettinen et al., New Technologies for Healthy Foods, pp. 71–83 (1997).
Habib et al., Sci. Pharm. vol. 49, pp. 253–257 (1981).
Mukhina e al., STN International, vol. 88, No. 7, pp. 1429–1430 (1977).
Mukhina et al., STN International, vol. 67, No. 9, pp. 587–589 (1967).
Tuomisto et al., *Farmakologia Ja Toksikologia,* pp. 526–534 (1982).
Ikeda et al., *J. Nutr. Sci. Vitaminol.,* vol. 35, pp. 361–369 (1989).
Heinemann et al., *Eur. J. Clin. Pharmacol.,* 40(Suppl 1), pp. S59–S63 (1991).
Mattson et al., *J. Nutr.,* vol. 107, pp. 1139–1146 (1977).
Herting et al., *Fed. Proc.,* vol. 19, pp. 18, (1960).
Takagi et al., *J. Am. Oil Chem. Soc.,* 47(10), pp. 326–330 (1980).
Qui et al., *Zhoggo Youzhi,* 21(3),pp. 14–18 (1996) (Abstract only).
Aoyama et al., *Yakagaku,* 34(1), pp. 48–52 (1985) (Abstract only).
Habib et al., *Arch. Pharm.,* vol. 323, pp. 401–404 (1990).

* cited by examiner

Primary Examiner—Deborah D. Carr
(74) *Attorney, Agent, or Firm*—Birch, Stewart, Kolasch & Birch, LLP

(57) ABSTRACT

The invention concerns dietary fat compositions that contain the hydroxy acid or dicarboxylic acid or amino acid esters of a phytosterol and/or phytostanol, or the mixed esters formed with the alcohols, polyols or polyol ($C_2 \ldots C_{22}$)-fatty acid esters of dicarboxylic acids or hydroxy acids, or the ($C_2 \ldots C_{22}$)-fatty acid esters of hydroxy acids.

29 Claims, No Drawings

USE OF ORGANIC ACID ESTERS IN DIETARY FAT

This application is the national phase under 35 U.S.C. §371 of PCT International Application No. PCT/FI98/00707 which has an International filing date of Sep. 9, 1998, which designated the United States of America.

The present invention concerns dietary fat compositions in accordance with patent claims 1 and 2, and food products in accordance with patent claim 6.

The invention also concerns plant stanol derivatives in accordance with patent claim 15, plant sterol and/or plant stanol dicarboxylic acid derivatives in accordance with patent claim 21, amino acid derivatives in accordance with patent claim 22, citric acid derivatives in accordance with patent claim 23, tartaric acid derivatives in accordance with patent claim 24, and plant sterol and/or plant stanol 3 (R)hydroxybutyric acid esters and their derivatives or salts in accordance with patent claim 25.

The method here described also concerns a method to make phytostanol esters in accordance with patent claim 26.

Plant sterols or phytosterols refer to the sterols appearing in the plant kingdom which closely resemble cholesterol in terms of structure. They are, like cholesterol in mammals, a certain structural component of external and internal membranes and thus essential constituents for the living functions of cells. Isolated plant sterols often appear in poorly soluble, crystalline form. The phytosterols appearing in nature are intrinsically fat solutions, however. Chemically, natural sterols are $C_{26} \ldots C_{30}$ alcohols, which have an aliphatic side chain in the C-17 position.

Cholesterol (5-cholestene-3-β-ol) and its hydrogenated form cholestanol ((3β, 5α) cholestane-3-ol) are found mainly in humans and animals. The sterols found in the animals, plants and mushrooms of marine organisms and sea-weeds form a wide variety of oxidation, double bond, methyl group substitution and C-17 side-group structures. The a configuration of the C-5 position when a hydrogen atom is linked to it is common to the natural sterols. A small number of plant stanols are also found in plants, the isolation of which is not economically profitable. Using a catalyst, phytosterols isolated in commercial applications can be hydrogenated into corresponding stanols.

Many phytosterols (independent of origin) are closely reminiscent of cholesterol in structure. The most well-known and the most studied are e.g. β-sitosterol (24β-ethyl-$\Delta^5$-cholestene (S24(β)-ethyl-$\Delta^5$-cholestene-3β-ol). The sterol that is characteristic of yeast and mushrooms is ergosterol (β24-methyl-22,23-dehydro-$\Delta^5$, $\Delta^7$-cholestadien-3β-ol=5,7,22-ergostatrien-3β-ol; provitamin D). The anticholesteric nature of the two first-mentioned phytosterols is generally known. It is possible that other sterols suited for this purpose can be found in nature, in addition to the β-sitosterol.

Plant sterols form part of our natural nourishment. The sources of plant sterols in our diet include plant oils and the margarines made from them, while phytosterols can also be found in grain products, soy beans and rice. The regular daily diet includes 0.2–0.3 g of plant sterols.

A certain physiologically important group of compounds is formed by relatives of the sterols, the cholic acids whose role in the food digestion organs is to act as a "biological soap", as an emulsifying agent of fat and as an absorption aid. Human bile contains several cholic acids conjugated with glycine and taurine (2-aminoethanesulphonic acid); glycine conjugates are those which mostly appear.

The effect preventing the cholesterol absorption of the β-sitosterol is assumed to be based on its ability to displace the cholesterol molecule in cholic acid/fat micelle. (Ikeda et al. 1989, J. Nutr. Sci. Vitaminol. 35:361–369). Many pieces of research into plant sterols have also shown that crystalline phytosterols do not dissolve very effectively in the micelle phase and therefore are not able to effectively prevent the absorption of cholesterol from the digestive tract. When water is present, solubility of phytosterols in plant oils is restricted to 2% at room temperature and to 3% at body temperature.

According to the observations of Heineman et al. 1991 (Eur. J. Clinic. Pharmacol. 40 Suppl. 1, p. 50–63), plant sterols inhibit cholesterol absorption only in fat-soluble form. A saturated form of β-sitosterol, β-sitostanol, inhibited cholesterol absorption in an infusion test substantially more effectively than the corresponding sterol (83% vs 50%). In general, the plant sterols are absorbed into the blood circulation poorly and the stanols not at all. Normally, the concentration of plant sterols in serum is $\frac{1}{300}^{th}$ part of the serum cholesterol level. In addition, according to the observations of Miettinen et al. (U.S. Pat. No. 5,502,045), an increase in sitostanol concentration in nutrition also lowers the measured β-sitosterol and campesterol concentration of the blood serum.

According to the observations of Mattson et al. (1977, J. Nutr. 107:1139–1146), it is probable that the molecules that really prevent cholesterol absorption are free phytosterol molecules which are hydrolytically released from their esters. This argument is supported by the fact that the cholesterol absorption lowering effect of the phytosterols does not depend on the length of the carbon chain of the fatty acid. Molar quantities of the fatty acid esters such as acetate, decanoate and oleate are equally as effective. In addition, the dicarboxylic acid esters such as phytosterol hemisuccinate lower the cholesterol content of blood as effectively as the phytosterol monocarboxyl acid esters.

The previously known methods to take advantage of the hydrophilic derivatives of β-sitosterol in food are based on a particular compound's glycosides obtainable from nature, e.g. the β-sitosteryl-β-D-glucoside. The carrier in the aqueous solution is, for example, lecithin, while the solvent may be isopropanol and the additive isopropylmyristate. In addition, the sterols' glycoside derivatives are bonded from the alcohol solution and/or emulsion to the starch (DE publication 2113215).

GB patent publication 938 937 describes a synthetic chemical, water-soluble phytosterol hemisuccinate-polyethyleneglycol condensate which has proved, in animal tests, to be effective in lowering blood cholesterol concentrations. The publication does not, however, state an opinion on the compound's hydrolytic decomposition in the system, or whether this kind of derivative is absorbed into the blood circulation or not. The compound is planned for use as a component of various juices, soups and soft drinks. It is clear, however, that the widespread use of the compound in food will be limited by the ethyleneglycol-based polyether component it contains and which is foreign to the human body.

Herting and Harris (1960, Fed. Proc. 19:18) have reported on a water-soluble soy sterol-2-carbamate glutaric acid $K^+$—salt which has been proved to lower blood cholesterol concentrations. Carbamates can be made by e.g. a reaction between chloroformates and primary amines. The carbamine acids are unstable and break up, releasing amine and carbon dioxide. The salts of carbamine acids are much more stable, however. As the chemical environment of food varies greatly, one can justifiably assume that there will be significant restrictions to the use of the compound. The publication does not indicate whether the presented compound is planned at all for use in foods.

A rise in the blood cholesterol levels is among the more important risk factors, along with smoking and higher blood pressure, in the spread of cardiac and vascular diseases. U.S. Pat. No. 5,502,045 describes the production of β-sitostanol fatty acid esters and their addition to food, especially as a part of edible fats in margarine, for example. The research carried out by Miettinen et al. 1995 (New Engl. J. Med. 333: 1308–1312) observed a decrease in the total serum cholesterol when the daily supply of plant sterol of the test individuals had stabilised at the 2–3 g level. The test used a saturated form of plant stanol, sitostanol, whose fat solubility had been increased by the esterification process. The tendency of the plant sterols to oxidate was reduced by the hydrogenation process.

A sitostane-3β-, 5α-, 6β-triol-3,6-diformiate (SU 574-450) classified as a stanol derivative has also been made from β-sitosterol. The compound has been proved to moderately lower the triglyceride content of the blood serum of rats and effectively lower the triglyceride content of liver (54% in guinea pigs). Tests measuring acute toxicity and performed on white male mice did not show toxicity at a 3.5 g dose per 1 kg of the animals live weight. The β-sitosterol used as a source material did not give a positive response in this test. The compound is planned for use in the prevention or treatment of fatty liver. The compound is fat-soluble. It does not dissolve very well in alcohol and not at all in water.

In patent publication EP 0 430 078 concerning cholesterols and phytosterols, a large number of (alkylene-ester/ether/amide functional hydroxyphosphine) coline hydroxide salts were made, which can be taken in doses orally in the form of tablets, capsules, emulsions, suspensions and in soluble form in order to lower the cholesterol content of blood plasma. The patent publication mentions as a synthesis intermediate stage a group of sterol and stanol hydroxy acid derivatives, namely cholest-5-en-3β-yl-(S)-2-hydroxypropionate, stigmasta-5.22-diene-3-β-yl-3-hydroxypropionate, stigmastanol-3-β-glycolate, stigmastanol-3-β-hydroxypropionate and stigmastanol-3-β-4-hydroxybutyrate (=γ-hydroxybutyrate). The aforementioned hydroxy acid esters were not used or tested, however, as nutritional additives to lower the cholesterol in blood. According to the patent publication, the synthesis of the compound group requires very powerful and toxic reagents such as phosgene, oxalyl chloride, trityl chloride or phosphoryoxy chloride, so that it can justifiably be assumed that their use is restricted to pharmaceutical preparations. The publication expresses no opinion on the behavior of sterol derivatives in the digestive system.

β-sitosterols have been fused with $HO_2C\ (CH_2)_n CO_2H$ (n=0–8) di-acids at a 40–50% supply and the liquid crystallization of the resulting compounds has been examined (Mukhina et al. 1977. Leningr. Khim-Farm. Inst., Leningrad USSR 24. Obshch. Khim. 47(6):1429–1430). The liquid crystals have been conventional applications of sterols e.g. cholesterol esters. No reports have been made, however, on the application of these compounds in lipid chemistry and the manufacturing process of food products.

Previously known are the 2-(2'-alkenyl) succinates made from cholesterols and phytosterols (EP 0554 897) and their use in cosmetics. The use of the $C_2 \ldots C_6$ hydroxy acid esters of phytosterols as components of hair shampoo compositions is known from patent publication JP 09194345. Phytosterols have also been esterified with lactic acid-oligomers and the resulting sterol esters have been used in formulations usable in e.g. hand creams and lip sticks (JP 58008098).

The use of phytosterols and their natural metabolites such as deoxycoline acid ascorbic, glutaric, tartaric and lactic acid esters for medical purposes other than the prevention or treatment of hypercholesterolemia is known from patent publication DE 19701264.

The β-sitosterol has also been esterified with 2,3-dihydroxy cinnamic acid and the antioxydative properties of the compound have been studied (Takagi, T. and Iida, T. J Am Oil Chem Soc 57(10):326–330 (1980).

Citric acid has previously been used to make fat-soluble glyceride derivatives, which observably have been effective antioxidants in plant oil and food which has a high fat content (Qiu et al. Zhogguo Youzhi. 1996,21,3,14–18). In addition, a synergetic antioxydative effect with tocopherol has been noticed in the case of citric acid, monoacyl glycerol citrate and ascorbic acid (Aoyma et al., Yakagaku, 1985.34 (1), 48–52.

In previously known methods a phytosterol or phytostanol derived from soy oil is dissolved in some edible medium (U.S. Pat. No. 5244887), which is used as a suspension or dispersion in food products. Generally known dispersing agents such as lecithin are used as additives.

Previously known techniques also include methods, in which hydrophobic sterols and stanols and their fatty acid esters are dissolved or fixed in e.g. fat and phospholipid emulsions (DE publication 4038385).

According to the the prior art, a fat-soluble β-sitosterol derivative is usually made from methyl esters by transesterification. Other generally known esterification methods are the reaction of sterols with fatty acid chlorides and anhydrides. Stanols, which are hydrogenated forms of plant sterols, can be used in the manufacture of esters.

The natural tendency of sterols to oxidize is reduced chemically by the hydrogenation process. In addition, the stereochemical structure of the molecule is altered by the hydrogenation process. In catalytic hydrogenation, the main product is the trans-fusion of the A, B rings, i.e. the hydrogen in the C-5 position is α-orientated, so that the molecule is almost flat. A small amount of C-5 position β-orientated hydrogen (cis-fusion) is obtained as a byproduct, whereafter the molecule has a curved shape. Trans-fusion is characteristic for natural hormones and cis-fusion for cholic acid.

According to the prior art, heterocyclic derivatives of β-sitosterol are manufactured by making the hemisuccinate of the β-sitosterol react with $SOCl_2$ and thiols, amines and phenols. The antilipemic properties of the esters obtained have been investigated, but there are no reports of the interaction between the ethanol/lipid soluble hemisuccinate of β-sitosterol with water soluble compounds (Arch. Pharm. (Weinheim. Ger.) (1990), 3232(7), 401–4).

The aim of the present invention is to synthesize new phytosterol and phytostanol esters, preferably β-sitosterol and β-sitostanol esters that have been modified so that the fat solubility of their derivatives has significantly increased in relation to free phytosterols and phytostanols. The aim of the invention is particularly to create tailor-made functional derivatives from phytosterols and phytostanols, that when dissolved in lipids can inhibit the absorption of cholesterol, and also increase the interaction between the hydrophobic lipid phase and water phase.

One risk factor in daily dietary intake is also the salt used in preservation, and regulation of taste and structural properties of industrially prepared food products, such as margarine, mayonnaise, and spreads, of which consumption (in excess quantities) is believed to be a significant factor in the development of hypertension.

Other commonly added ingredients to fat-containing food products include emulsifiers, thickeners, antioxidants, acidity regulators, and aromatic supplements. Food products may also contain colors, such as β-carotene, and vitamins, such as vitamin A and D.

The aim of the present invention is also to improve the structure, taste and preservation of dietary fat products.

The invention is based on the ability of the HLB relationship (Hydrophilic Lipophilic Balance) of phytosterol or phytostanol, preferably β-sitosterol or β-sitostanol esters, to be regulated so that the compound is soluble in lipid and ethanol, and dispersible in water. The invention is also based on the fact that attaching a chemically very different group to a phytosterol or phytostanol molecule decreases the characteristic crystallization of sterols and stanols, e.g. in a plant oil solution. According to the invention, β-sitosterols or β-sitostanols can be made to react with aliphatic hydroxy acids, ketoacids, dicarboxylic acids or amino acids, or their derivatives, to form β-sitosterol or β-sitostanol esters with the aforementioned acids. The esters formed are lipid soluble, and improve the surface chemical mixability of fat and water.

The compounds according to the invention have a highly lipophilic sterol/stanol structure and a hydrophilic structural unit.

More precisely, it is characteristic for the phytosterols and phytostanols according to the invention that the hydroxyl group in the 3β-position in the sterol/stanol ring is esterified with a polar substituent, for example a dicarboxylic acid, hydroxy acid, amino acid, or with the oligomeric polyesters of the aforementioned acids or with mixed esters of the aforementioned dicarboxylic acids or hydroxy acids, with either an alcohol component or fatty acid component.

Significant advantages are achieved with the invention. Polar, lipid-soluble phytosterol and phytostanol derivatives according to the invention can be utilized to emulsify lipids in water; in other words, the compounds work using a mechanism that is almost the same as the body's own lipid emulsifying mechanism. The present invention is based on the observation according to which, for example phytosterol dicarboxylic acid hemiester, plant oil, and water form a stable emulsion when mixed. Thereby, compounds according to the invention are excellent for application in the preparation of e.g. light spreads, mayonnaise, and salad dressings.

Compounds according to the invention may be added to products that typically contain plant oil, such as cooking oil, margarine, light spreads, mayonnaise, chocolate, and ice cream, in comparative concentrations (preferably 0.1–10% of total fat mass), in comparison to already commercialized phytostanol fatty acid ester-containing dietary fat preparations. Products according to the invention can also be added to industrially prepared fat emulsions, such as cream liqueur bases.

More precisely, dietary fat constituents according to the invention are those constituents defined in the characterizing part of patent claims 1 and 2, and the food product defined in the characterizing part of patent claim 6.

The invention differs significantly from previously known solutions in which sitostanol, which lowers blood cholesterol levels, is present as a fatty acid ester in one component of dietary fat. The energy content of the dietary fats containing compounds according to the invention is significantly lower (5–10%) than the sitostanol fatty acid esters.

The phytosterol and phytostanol dicarboxylic acid and hydroxy acid esters according to the present invention are hydrolyzing esters, whose characteristics can be assumed to differ from those stanol esters that are already known and have been commercialized. Factors affecting the different rates of hydrolysis of different esters are known from general organic chemistry. Steric and electronic factors are the most important. A substituent group in the side chain of an ester that attracts electrons, for example, increases the speed of hydrolysis. On the other hand, a substituent, such as an alkyl group, that donates electron density in the side chain decreases the speed of hydrolysis. Therefore, for example, poly(hydroxy succinate) is hydrolyzed faster than poly(2-S-hydroxy propionate).

Plant sterol and/or plant stanol esters according to the invention can be added, for example, to food products containing plant oil, such as mustards, salad dressings, and peanut butter. Citric and/or tartaric acid, or their salts, are often added to the aforementioned food products. Phytosterol citrates, lactates or tartrates according to the invention can also be used to achieve the same effect in these food products. The unhealthy effects of a meal that is high in fat and cholesterol can be counteracted with the use of these products.

Dissolved in plant oil, the plant sterol and/or plant stanol derivatives according to the invention can also very well be added to e.g. industrially produced canned fish, of which two common examples are tuna or sardines preserved in plant oil.

Of the compounds according to the invention, phytosterol and phytostanol lactic acid esters (-mono-L-lactate and -poly[L-lactic acid]) are lipid soluble compounds that have a potentially wide range of application, and whose range of application ranges from margarine to various milk products. As the compounds according to the invention have been found to dissolve and be excellently compatible with various fat dispersions, there is no reason not to add the compound in question, preferably lactic acid esters, to e.g. cream, which can then be used to make ordinary processed products, such as soured whole milk and sour cream.

In terms of its physical properties, β-sitosterol and β-sitostanol-oligo-/poly-L-lactic acid ester is a viscose liquid between 50–100° C., which can be dispersed in water with common methods, if necessary. If desired, the regular emulsifiers used in food products, such as sugar lipids and lecithin, can be used as additives, and proteins, modified starches, hydrolyzed carboxy methyl cellulose are some examples of substances that can be used as protective colloids.

Compounds according to the invention are soluble and/or dispersable in water, ethanol and lipids, so that compounds according to the invention can at the same time be dissolved/dispersed in water and ethanol and dissolved in the fatty component of the product.

Compounds according to the invention can be e.g. in an approx. 6% fat-containing cream liqueur dissolved simultaneously both in a water/alcohol solution and in the fatty component of the product.

Compounds according to the invention dissolve and/or disperse in water, ethanol and lipids, and also acetic acid, so that compounds according to the invention can at the same time be dissolved/dispersed in water and acetic acid and dissolved in the lipid component of the product.

Chemically, plant sterol and plant stanol esters according to the invention can be classified as hydrolyzing esters. Even though we are not able to commit to any theory regarding the action mechanism of the compounds, we can justifiably assume that the compounds according to the invention act as substances that lower the serum cholesterol level, and that, in the body, the carboxylic acids act in accordance with their characteristics.

The sterol or stanol derivatives according to the invention is based on natural compounds, whose use in food products as safe techno chemicals and as materials suitable for a biological environment is anyway widespread. In addition, they can be synthesized economically and with a minimum number of side products. Here, processes producing side products mean, for example, the acid chloride method, in which 1 mole of sterol reactant produces 1 mole of hydrochloric acid, and the anhydride method in which the mole amount of reactant produces the same number of moles of carboxylic acid, or the reaction of a sterol with an enol ester (e.g. propene acetate) which produces the same number of moles of acetone.

Compounds according to the invention, e.g. citrate and tartrate, are examples of a group of organic esters which are known for being difficult to absorb. In large doses, these organic ions have been used as osmotic laxatives. (Tuomisto, J. and Paasonen, M. 1982. Pharmacology and Toxicology (in Finnish). Kandidaattikustannus Oy. Helsinki. pp. 526–529).

The invention will now be explained in more detail with the aid of the following detailed description and with the reference to a number of working examples.

The aim of the invention here presented is to produce a polar ester from β-sitosterol or β-sitostanol that is soluble in dietary fats, and which has a carboxylic acid component that is a natural compound found in the body and/or is found and/or is useable in food products, preferably succinic acid, glutaric acid, ketoglutaric acid, malic acid, tartaric acid, citric acid, lactic acid, 3(R)-hydroxybutyric acid or an amino acid derivable from proteins, or a derivative of these.

The hydroxy acid ester of a phytosterol and phytostanol can also be an oligomeric polyester, that is defined by the more general definition polyhydroxy alkanoate. In this case, poly(L-lactic acid) is also classified as a polyhydroxy alkanoate.

Hydroxy acid esters of phytosterols, such as citrate and tartrate, can be modified if desired by e.g. mixed esterification, when either the COOH-group is esterified using an aliphatic alcohol, polyol, polyol (C2 ... C22) fatty acid ester, or a free OH-group is esterified with C2 ... C22 fatty acids.

If required, hemi esters of phytosterol and phytostanol can be modified by mixed esterification with aliphatic alcohol, polyol, or with a polyol(C2 ... C22) fatty acid ester.

The most preferred polyol component is glycerol, though it can also be ascorbic acid.

Generally speaking, it is characteristic for the invention that the polarity of the β-sitosterol/stanol esters is increased by increasing the number of heteroatoms, such as N and O in the molecule. Even more generally, it is characteristic for the invention that the substituent in the C3 position of the phytosterol/stanol decreases the crystallization of the derivative, compared to an unsubstituted plant sterol or plant stanol, and thus increases the lipid solubility of the compounds in question, or the stability of the fat solutions. Suitable functions in the side group include ester, ether, carbonyl, carboxyl, amine and amide and/or e.g. combinations of these functional groups.

According to certain preferred embodiments in the present invention, phytosterols and phytostanols are specifically esterified with lactic acid, citric acid, succinic acid or glutaric acid.

Particularly preferred compounds according to this invention include the esters formed by plant stanol with the acids listed above, and their derivatives.

Particularly preferred compounds for addition to dietary fat products are the dicarboxylic mixed esters of plant sterols and plant stanols according to this invention, such as ethyl β-sitosterol succinate, β-sitosterol or β-sitostanol lactate, β-sitosterol or β-sitostanol succinate lactate, β-sitosterol or β-sitostanol hydroxy butyrate, β-sitosterol or β-sitostanol tartrate, β-sitosterol or β-sitostanol succinyl 3(R)-hydroxy butyrate and acylated, mix esterified citrates.

Dicarboxylic acid derivatives of plant sterol or plant stanol have the formula:

in which

S = a plant sterol or plant stanol

R = C2 ... C6 carbon chain;

Y = H or $C_2H_5$

In this invention, preferred compounds are, for example, sterol succinate lactic acid condensate (II), sterol succinate-3(R)-hydroxy alkanoate condensates (III), such as sterol succinate-3(R)-hydroxy butyric acid condensate (IV)

$Y_1$ = H or $C_2H_5$ or

$Y_2$ = H or $C_2H_5$, $R_1$ = $C_2$ ... $C_6$ alkyl or

$Y_3$ = H or $C_2H_5$

According to this invention, amino acid esters of phytosterols or phytostanols are also preferred compounds, and have the formula:

S = plant sterol or plant stanol

R = H or the structure appearing in natural L-amino acids

According to this invention, citric acid derivatives of phytosterols or phytostanols, are also preferred compounds, and have the formula:

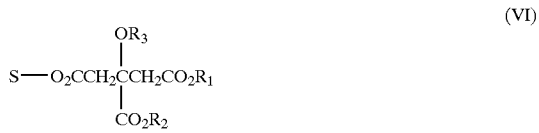

S = plant sterol or plant stanol $R_1$ = $R_2$ = H and $R_3$ = C2 ... C22 carboxyl acid residue or $R_1$ = $R_2$ = —$C_2H_5$ and $R_3$ = H or $R_1$ = $R_2$ = —$C_2H_5$ and $R_3$ = C2 ... C22 carboxyl acid residue or $R_1$ = $R_2$ = —$CH_2CHOHCH_2OH$ and $R_3$ = H or $R_1$ = $R_2$ = —$CH_2CHOHCH_2OH$ and $R_3$ = $OCCH_3$ Therefore, preferred citric acid esters are, for example, steryl acyl citrate, steryl diethyl citrate ($R_1$ = $R_2$ = $C_2H_5$, $R_3$=H), steryl acyl diethyl citrate ($R_1$=$R_2$=$C_2H_5$, $R_3$=C2 ... C22 carboxylic acid), steryl citrate diglycerol ester ($R_3$=H, $R_1$=$R_2$=—$CH_2CHOHCH_2OH$), steryl acetyl citrate glycerol ester ($R_3$=$OCCH_3$).

According to this invention, tartaric acid derivatives of phytosterols or phytostanols, are also preferred compounds, and have the formula:

$$S—O_2CCH(OR_1)CH(OR_2)CO_2Y \quad (VII)$$

S=plant sterol or plant stanol $R_1$=$R_2$=Y=H;

or $R_1$=$R_2$=H and Y=$C_2H_5$ or $R_1$=$R_2$=acyl $C_2$ ... $C_{22}$ and Y=H or $R_1$=$R_2$=acyl $C_2$ ... $C_{22}$ and Y=$C_2H_5$ The aim of the invention is to provide a method for the use of tailor-made functional plant sterol and pant stanol esters as a cholesterol-lowering component in dietary fats and fat-containing milk products or alcoholic beverages. In addition, the aim of the invention is to improve the quality, preservability, and processability of these products.

β-sitosterol and/or β-sitostanol esters can be dissolved in animal fats, plant oils or 4–40% fat emulsions, in which the fat proportion preferably contains 1–10 weight-% of compounds according to the invention. Alternatively, liquefied β-sitosterol or β-sitostanol esters (preferably lactic acid esters) can be dispersed in water (preferably to form a 10–40% emulsion), and added in the required concentration to the food product being prepared.

"Plant sterol and/or plant stanol" refers to sitosterol, stigmasterol, campesterol, brassicasterol, cycloartenol, 24-methylene cycloartenol and cyclobranol and/or their hydrated forms, and mixtures, and which have a serum cholesterol lowering effect. Even though the terms â-sitosterol and/or β-sitostanol are used in conjunction with this invention, it also includes other plant sterols and/or stanols which have a cholesterol-lowering effect.

By a "dicarboxylic acid" here is meant an organic acid that has two carboxyl groups (—COOH). Suitable dicarboxylic acids in this invention are, for example, glutaric acid and its derivatives, and succinic acid.

In an esterification reaction, the —OH group of the carboxylic acid is released and forms water, while the alcohol, in this case β-sitosterol or β-sitostanol, reacts with the carboxylic acid residue to form an ester.

By a "hemi ester" here is meant that only one of the dicarboxylic acid's —COOH groups has reacted with the alcohol.

By a "ketoacid" here is meant an organic acid that contains a keto-group in the hydrocarbon structure of the acid. Ketoglutaric acid is an example of a ketoacid.

By a "hydroxy acid" here is meant an organic acid that contains a hydroxyl group in the hydrocarbon structure of the acid. In this invention, suitable hydroxy acids include malic acid, tartaric acid, citric acid, lactic acid, and 3(R)-hydroxy butyric acid.

By an "amino acid ester of β-sitosterol" is meant, for example β-sitosterolglycinate (=β-sitosterol amino acetic acid ester). The amino group may, of course, have originated from any amino acid, poly(amino acid) or peptide.

"Phytosterol/stanol polyhydroxy alkanoates" refers to the following, common chemical structures:

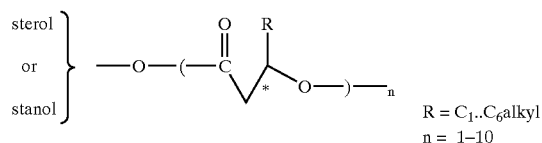

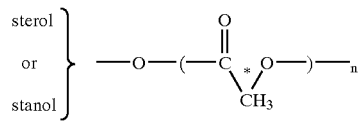

A "β-sitosterol oligo/polyester" refers to the formation of a β-sitosterol ester from more than one hydroxy acids or with a dicarboxyic acid or amino acid. One example of such an ester is the β-sitosterol succinate (acyl glycerol) ester.

"Polyol" refers to a compound containing at least two hydroxyl groups. Glycerol is an example of a polyol.

By "poly/oligo esters of β-sitosterol or β-sitostanol" is meant that β-sitosterol has been esterified with, for example lactic acid polymer which has at least two L-lactic acid units.

By "dietary fats" is meant animal or milk fats adapted for use as food, plant oils, such as rape seed, sunflower, olive and palm oil, either in their natural form, or chemically modified.

According to this invention, the fat proportion of a food product can contain 0.01–10 weight-% of phytosterol/stanol, preferably the hydroxy acid, dicarboxylic acid, or amino acid derivatives of β-sitosterol or β-sitostanol, or mixtures of the aforementioned derivatives.

Fat-containing food products refers to such food products of which one component is fat derived from either animal or plant sources. Such food products are, for example, chocolate, cream liqueur, ice cream, butter, margarine, sandwich spreads, mayonnaise, salads containing mayonnaise, salad dressings, mustards, and preservatives, as well as various milk products. Food products containing fat also includes fat-containing alcoholic beverages.

It is characteristic for the method according to the invention that β-sitosterol or β-sitostanol is esterified in a one-step process with a dicarboxylic acid, hydroxy acid or amino acid, so that there will be at least one carboxylate, hydroxyl, or amino group, or a combination of the aforementioned functional groups in the ester's side chain. Also characteristic of the method is that the sterol/stanol esters are soluble in fats or fat emulsions, in which form they can be used as a structural component of food products prepared from fats or fat emulsions.

In principle, the amino acid esters of β-sitosterol or β-sitostanol can be made using any generally known peptide-synthetic method, for example, the activated esters (p-nitrophenyl, hyrdoxy succinic imide, pentachloro phenyl esters) of amino acids together with an N-protection (for example, BOC=tert-butyl oxycarbonyl and benzyl oxycarbonyl). It is preferred to use benzyl protection, because as a powerful protective group it permits, for example, transesterification when making sterol esters. Benzyl protection is particularly preferred for a secondary amino group. L-proline and 4-hydroxy-L-proline are examples of such groups. In addition, benzyl protection can be removed by hydrogenation.

Compounds according to the invention are manufactured by combining the reactants in the desired molar ratios (batch process) and removing water (preferably azeotropically or by molecular sieving), alcohol, or other volatile condensation products from the reaction mixture by distillation, giving a high yield of esters that are soluble in lipids or ethanol.

The esterification of a β-sitosterol or β-sitostanol is carried out at a high temperature 110–280° C., either by a direct esterification method, in which water is removed azeotropically from the reaction mixture, or by transesterification, when some volatile condensation product is distilled from the reaction mixture. Hemiesters (for example, succinate and glutarate) are more economically manufactured directly from the corresponding cyclic anhydride at a temperature of 90–200° C.

In esterification based on the removal of water, it is technically possible to use numerous azeotrope systems, advantageously hydrocarbons, such as cyclohexane, toluene or technical xylene. The task of the aforementioned solvent in the reaction mixture is not only water removal, but also the control of the temperature of the reaction mixture. More precisely, the temperature of the reaction mixture is controlled by adjusting the ratio of the weights of the solvent and the reactants to 15–50% of the mass of the reactants.

In esterification at a temperature of less than 140° C., it is preferred to use cyclohexane or toluene as the solvent and xylene at higher temperatures. Technically, it is also preferred to allow water, which is possibly in the reactants, to leave as an azeotrope, before arriving at the reaction temperature; thus a separate drying stage for the reactants may be unnecessary.

In direct esterification, it is also preferred to use a strong acid as the catalyst, which need not be removed from the reaction mixture. Esterification with cyclic anhydrides can also be carried out thermally without a catalyst. Esterification can be carried out with cyclic esters, such as lactons, glycolides and lactides, using the conventional methods known to the literature of chemistry.

According to one preferred embodiment, phytosterol/stanol oligomeric lactates are manufactured from compounds according to the invention by non-catalytic esterification at a temperature of 155–120° C., starting from a 90% L-lactic acid water-based solution and phytosterols or phytostanols, with toluene acting to form a water azeotrope. Under such weak reaction conditions, it is justified to assume that the risk of racemization of the lactic acid is very small.

The catalyst used in transesterification can be equally well strong acids (TsOH (=paratoluene sulphonic acid), $H_2SO_4$, $H_3PO_4$, etc.), alkalis (NaOH, KOH, NaOEt, t-BuOK (=potassium tert-butylate) etc.) or the generally used weak Lewis acids. From the point of view of the intended application of the present invention, it is not, however, preferred for metals to appear in the reaction mixture, except for Na, K, Ca, Mg. Generally, it is not preferred from the point of view of the intended application for halogenides to appear in the reaction mixture.

According to one preferred embodiment of the invention, β-sitosterols are generally hydrogenated using known methods to form respective stanols, and the esterification reactions are only carried out after this using stanols.

According to instructions in literature, (Fieser & Fieser, 1967. Reagents for Organic Synthesis, Vol. 1. p. 799) sterols can be hydrogenated, at a high yield and in moderate reaction conditions, to form stanols (0.02% $PtO_2$ of the mass of the sterol. EtOAc, $H_2$/103kPas, 40–5° C., ½ h, acid co-catalyst). The reaction products are 88% sitostane-3β-ol, 3.4% sitostane-3α-ol and 0.9% sitostane. In addition to this, 1.6% sitostane-3β-acetate is obtained from the exchange reaction.

According to one preferred embodiment of the invention, β-sitosterols are esterified and sterol esters are hydrogenated to form stanols. Because, for example sterol lactates are highly soluble in alcohol, a sterol ester can be hydrogenated to directly form its respective stanol ester. This achieves the significant advantage that hydrogenation can be carried out at room temperature. As the solubility of phytosterol in alcohol at 20° C. is ≦1%, phytosterols cannot be hydrogenated at similar conditions to form stanols. Sterols must be hydrogenated to form stanols in ethanol at 65–77° C.

Sterol esters that are soluble in acetic acid can be hydrogenated in concentrated acetic acid to form stanols. It is practical for the hydrogenation to be carried out directly in an ethanol or acetic acid solution, which will be used later in the manufacture of beverages or vinegar products.

A large number of heterogenic and homogenic hydrogenation catalysts and reagents are known in organic chemistry (e.g. March, J. advanced Organic Chemistry, Reactions, Mechanism and Structure, $4^{th}$ edition. Chapters 5–9 and in the notes to them), by means of which the double bond of a sterol can be reduced without converting the functional group of the 3β-substituent, which can be, for example OH, COOH, CONHR or COOR.

The polarity of the sterol/stanol esters described above is an extremely useful property. It is characteristic of compounds according to the invention, e.g. β-sitosterol dicarboxylic acid hemiesters and citrates that in lipid solutions (e.g. 2.5–5% of the fat component) they promote the mixing of the lipid and the water. This was found to have a preferred effect on, e.g. the structure and taste of light spreads, which in this case means that the product is less oily; excellent to spread, at both room and refrigerated temperatures. The prepared light spread also lasted better than the comparative sample when heated to 45° C. for up to 4 hours. By improved thermal resistance is meant that after 2 hours at 45° C., more oil had separated from the comparative sample than from the sterol-containing sample. Over the next 2 hours, the separation of oil from the comparative sample continued. In the sterol-containing spread, however, negative change had ceased. Changes in the sterol ester-containing sample, in which the fat component contained 5% plant sterol hemisuccinate, were almost reversible; in other words, the structure of the sample returned to almost the same upon mixing the sample after it had returned to room temperature.

Generally, a 2.5–10% proportion of compounds according to the invention, e.g. sterol lactates, citrates, and hemisuccinates, in the fat component of the mass of dietary fat products, such as light spreads and mayonnaise, have been found to have no negative effects. Instead, it was surprisingly found that in most cases added salt can be left out of the product family in question, without the smell, taste or structure of the product being adversely affected in any way. In addition, sensory evaluations showed that sterol citrates emphasize e.g. the wine vinegar and mustard aromas contained in mayonnaise.

Just as with dietary fat products, the compounds according to the invention were found to be suitable for chocolate products. The fatty component of these products can contain compounds according to the invention e.g. 2–5% without any adverse effect on the product's structure or taste.

For an alcoholic beverage, which in this case means a cream liqueur, the results were consistent with the previously described products. The fatty component of the product can contain, for example 2–4 weight-% of compounds according to the invention without changing the characteristic smell or taste of the product.

A significant advantage for compounds according to the invention, and their use as a component in various daily dietary fat preparations, chocolate confectionery, or alcoholic beverages, is that phytosterol/stanol hydroxy acid esters are potential antioxidants on the basis of what is already generally known e.g. about esterified citrates.

The following examples illustrate the invention. They do not, however, limit the patent's scope of protection.

The starting material for compounds according to the invention was a plant sterol mixture (Weinstein Nutritional Products), which was composed of 45–55% β-sitosterol, 20–30% campesterol, and 15–25% stigmasterol.

EXAMPLE 1

The lactic acid used in the formation of the lactate was Purac heat-stable L-lactic acid, with a lactic acid content of 88%. The citric acid was a commercial citric acid monohydrate (food product quality). In the preparation of the derivatives, the azeotropic solvent used was technical-grade toluene, and the solvent used in the hydrogenation of sterol was ethanol (Primalco Oy 96.5 volume-% ethanol). The hydrogenation catalyst was 5% Pd/C (Aldrich).

EXAMPLE 2
Hydrogenation of β-sitosterol 5.0 kg of ethanol (96.4 volume-%) and 0.2 kg of β-sitosterol was mixed in a 10-liter reactor. The reactor was flushed thoroughly with nitrogen twice, after which 1–3.5 g of hydrogenation catalyst (Pd/C) suspended in ethanol was added to the reactor. After this, a vacuum was created in the reactor twice. Hydrogen was fed into the reactor while the temperature was increased slowly to 54–57 °C. When it appeared that hydrogen was no longer being consumed (the pressure did not decrease), the hydrogen pressure was released, the reactor was flushed with nitrogen, and the reaction mixture was filtered while hot to remove the catalyst.

Once the reaction mixture had cooled, stanol began to crystallize from the solution. The solvent was evaporated to approximately half the original volume, and the remaining stanol was crystallized by cooling the reaction mixture at 10° C. The product was air-dried at room temperature. Individual hydrogenation tests showed process technical differences, which have been recorded in Table 1.

Hydrogenation was carried out in a 10-liter BUCH pilot reactor. The vacuum-nitrogen flushing cycles were carried out before the reaction. In the hydrogenation experiments, hot water and/or steam heating were used instead of thermal oil. $H_2$ flow measurement was used.

TABLE 1

| Test no. | sterol (kg) | EtOH (kg) | Pd/C10% Pd (g) | reaction conditions |
|---|---|---|---|---|
| 1 | 0.2 | 3.9 | 3.0 | $H_2$: 1–2 bar, 43° C., 4h, 4 × $H_2$ charge < 2 bar |
| 2 | 0.2 | 4.7 | 3.0 | $H_2$: 1–2 bar, 77° C., 4h, 4 × $H_2$ charge < 2 bar |
| 3 | 0.2 | 4.7 | 3.0 | $H_2$: 1–1.5 bar, 77° C., 3h, continuous $H_2$ feed |
| 4 | 0.2 | 4.7 | 1.5 | same as previous |

Composition of the products of hydrogenation:
1. 77% stanols, remainder sterols, no stigmastane/campestane
2. 78% stanols, no sterols, remainder stigmastane/campestane
3. 84% stanols, no sterols, remainder stigmastane/campestane
4. 93% stanols, no sterols, remainder stigmastane/campestane

EXAMPLE 3
Preparation of β-sitosterol Hydrogen Succinate

The following substances were allowed to react:
9.0 g β-sitosterol
2.15 g succinic acid anhydride
1.7 g pyridine
20 ml toluene The mixture was heated intermittently for 5 h. The toluene was evaporated using a vacuum. 2.5 ml of 1N HCl dissolved in 50 ml ethanol (96.4 volume-%) was added. The white precipitate formed was filtered, filter-washed with a 2:3 water-ethanol solution, and finally with distilled water. The product was dried by gentle heating.

EXAMPLE 4
β-sitosterol Citrate

The following substances were allowed to react:
50.0 g β-sitosterol
66.0 g citric acid monohydrate
100.0 ml xylene
+an acid catalyst, such as paratoluene sulphonic acid, $H_2SO_4$ or $H_3PO_4$ The mixture was isothermally heated for 6 hours in nitrogen atmosphere at 145° C., or until the xylene circulating in the water separator clarified in the final stage of esterification. The cooled reaction mixture was a viscous reddish liquid. The xylene was evaporated by vacuum evaporation. The waxy reaction product was dissolved in ethanol to a concentration of 5–30 weight-%. The reaction product was recipitated as a yellowish wax using cold precipitation at a temperature of +/−0–40° C.

EXAMPLE 5
β-sitosterol Citrate; Heterogeneous Reactions

Sterol, citric acid and toluene were mixed in a flask. The temperature of the reaction mixture was increased to boiling point, and the water collected with a water separation device, to monitor the progress of the reaction. A catalytic amount of phosphoric acid was added to the reaction mixture. In the early phase, the reaction mixture was heterogeneous, but as the reaction progressed it changed into a one-phase mixture. After the reaction, the toluene was evaporated from the mixture using a rotavapor, and the product was dried in a vacuum oven at 40–60° C. Table 2 shows, for the various experiments, the reaction conditions, the molar ratios of the starting materials, and the quantity of reaction water formed.

TABLE 2

| Experiment | Starting materials (g) | molar ratio | reaction conditions | reaction water, ml (in mols) |
|---|---|---|---|---|
| 1 | 100.0 sterol 149 citric acid | ⅓ | 12 h: 110° C., 3 h: 135–149° C. | 9.0 ml (0.5 mol) |
| 2 | 100.0 sterol 149 citric acid | ⅓ | 32 h: 110° C., 3 h: 140–150° C. | 20.0 ml (1.1 mol) |
| 3 | 100.0 sterol 184 citric acid | ¼ | 11 h 30 min: 110–120° C. | 11.0 ml (0.6 mol) |
| 4 | 140 citric acid (blank) | | 40 h: 110° C. | 10–1.5 ml |

EXAMPLE 6
β-sitosterol Citrate from Citrate Condensation 185 g of anhydrous citric acid and 300 ml toluene were mixed in a 1000 cm$^3$ flask, and 8 ml of water was azeotropically distilled from the reaction mixture during the overall reaction time of 36 hours. The amount of water collected during this time represents 45% of the total number of moles of citric acid. Next, 100 g of β-sitosterol (which represents 0.24 mol) was added, and the water distillation was continued until 8–10 ml more had been collected, after which the reaction was finished. The raw product was treated as described in the previous example. Using this method, more alcohol-soluble citrates were obtained than in experiments 1,2 and 3 of the previous example.

EXAMPLE 7
Di-(β-sitosteryl)Citrate; Heterogeneous Reactions

Di-β-sitosteryl citrate is formed in a heterogeneous reaction between citric acid and β-sitosterol, at the same reaction conditions as described in the previous section. The compound is separated from the sterol monocitrate on the basis of solubility, using ethanol extraction. The method is based on the fact that the solubility of sterol monocitrate in ethyl alcohol is ten times that of di-β-sitosteryl citrate.

EXAMPLE 8
Preparation of Sterolacetylcitrate in a Homogenous Reaction Mixture Crystalline citric acid dihydrate (100 g, 15.7% hydrate water), 100% acetic acid (400 g) and acetic anhydride (156.5 g) was mixed in a 1 liter volumetric flask, and heated intermittently for 4 h at 120° C. Next, 50 g of β-sitosterol was added to the reaction mixture. The solution was heated intermittently for 4–5 h at 120° C. and allowed to cool at room temperature. The white precipitate was separated by filtration. The filtrate was diluted with 5 liters of water, and a yellowish precipitate was formed. The precipitate was filtered and washed in the filter with water. The product was dissolved in ethanol. The light colored precipitate (1.3 g) was filtered. The actual reaction product (yield 16 g) was obtained as waxy crystals after the ethanol was evaporated. The advantage of the preparation method described in this example is that the product can be produced in acetic acid without using other solvents.

EXAMPLE 9
Citric Acid Ester Sterol Condensate
Ethyl-β-sitosteryl Citrate

The following substances were allowed to react:

50.0 g β-sitosterol 66.0 g triethyl citrate

+catalyst such as paratoluene sulphonic acid, $H_2SO_4$, $H_3PO_4$, NaOH, KOH, NaOEt, t-BuOK or Lewis acids Ethanol was distilled from the reaction mixture using nitrogen gas at 160–250° C. for 3–6 h. The cooled reaction mixture was a viscous reddish liquid. The sterol ester was purified by cooling the 5–15 weight-% ethanol mother liquor of the reaction product to a temperature of +/−0−−40° C., when a light-colored product was obtained as a waxy precipitate.

EXAMPLE 10
Citric Acid Reaction with β-sitosteryl, Non-catalyzed I 25.0 g β-sitosterol, 50.0 g citric acid monohydrate and 150 ml toluene were heated intermittently for 6 h at 110–112° C. At this point, approximately 5 ml of water was collected in the water collector.

The surplus, unreacted citric acid was removed from the cooled reaction mixture by filtration, the citric acid was washed in the filter with toluene, and the filtrates were combined. The toluene was removed by distillation at 60–80° C. at a reduced pressure in a vacuum (29 mmHg). The yield was approximately 30 g.

EXAMPLE 11
Citric Acid Reaction with β-sitosteryl, Non-catalyzed II 50.0 g β-sitosterol, 100.0 g citric acid and 200 ml cyclohexane were heated intermittently using a water separator for a minimum of 20 hours. The hydrate water (approximately 8.5 ml) was separated at the start of the heating. After this, water formed very slowly (theoretically 2.2 ml).

Heating was continued until the small droplets of water disappeared from the cyclohexane returning from the condenser, or at least until 1.5 ml of condensation water had been separated.

Initially, the cyclohexane was removed by distillation at normal pressure, and then at a reduced pressure (approximately 30 mmHg). Any remaining solvent residues in the solidified reaction mixture were evaporated in a vacuum (0.3 mmHg).

The unreacted citric acid was removed by extraction with water at room temperature. The light-colored, yellowish, poorly soluble precipitate was filtered and dried. The yield was 60.0 g. The raw product was purified by dissolving it in 1000 ml 96.4 volume-% ethanol at room temperature. Any unreacted β-sitosterol was separated from the ethanol solution by filtration.

Useable product was obtained from the uncatalyzed β-sitosterol reaction with citric acid, showing the usefulness and development potential of this preparation method.

EXAMPLE 12
Acid Catalyzed Citric Acid Reaction with β-sitosterol

The following substances were allowed to react:

50.0 g β-sitosterol 33.0 g citric acid monohydrate 54.0 g cyclohexane 2.9 ml of hydrate water was distilled from the reaction mixture at a temperature of 80–82° C. At this point, the cyclohexane began to circulate clear in the water trap. The esterification stage was started by adding 200–300 mg of orthophosphoric acid. Water distillation was continued for 8 hours at the original temperature, during which time 2.5 ml more water collected (theoretically 50.0 g/414 gmol$^{31}$ 1×18.0 gmol$^{-1}$=2.2 ml $H_2O$). The reaction mixture, which was fluid during heating, changed into a viscous mass.

Using this method, at least 44% of the sitosterol would have reacted to form alcohol-soluble citrates.

EXAMPLE 13
β-sitosterol Salts

While stirring, drops of 25% ammonia solution were added to the raw product (β-sitosterol citrate from example 12), which was a 96.4% volume-% ethanol solution containing 6–10 weight-% of citrate, when a white, cheese-like precipitate began to form immediately. The precipitate was collected on the filter using a partial vacuum and was flushed with cold ethanol. Next, the precipitated sterol citrate ammonium salt was dried in a vacuum using gentle heat. The dry product was a white powder.

The composition of the primary elements was 60.6% C and 8.1% H, with an approximate molecular formula of $C_{41}H_{64}O_{13}$, i.e. a sterol substituted citrate dimer.

The composition of the primary elements of the ammonium salt was 62.05% C, 9.04% H, 3.63% N, which is represented by the molecular formula $C_{41}H_{68}O_{13}N_2$, i.e. a sterol substituted citrate dimer ammonium salt.

Potassium salt is prepared similarly from the β-sitosterol citrate in example 6, by adding 0.5 N KOH.

EXAMPLE 14

A mixture containing 5.0 g of di-betasitosteryl citrate suspended in 300 g of water and 0.4 g of KOH was heated at 90–100° C. for 5 h, after which the white precipitate was allowed to settle. Titration of the clear liquid with a 0.5 N HCl solution and phenolphthalein indicator to neutral showed that 86% of the KOH had reacted with the sterol. 0.9 g of dissolved material, was observed in the water solution and precipitated when the water solution was made strongly acidic with the HCl solution. The reaction showed that partial hydrolysis of the disterol citrate produces a water soluble sterol monocitrate potassium salt, from which the corresponding carboxylic acid is released by a strong acid.

EXAMPLE 15
β-sitosterol Tartaric Acid Condensate

Initially, the following substances were reacted:

50.0 g β-sitosterol 36.1 g (+) tartaric acid 57.0 g xylene solvent

300 μl $H_3PO_4$ catalyst

Water was azeotropically distilled from the reaction mixture at 146° C. for 12–13 h. After cooling, the reaction mixture was a light-colored half-crystalline mass from which the xylene was removed using vacuum evaporation. After removal of the xylene, the product was kept in vacuum at 80–90° C. in order that all xylene residues would be removed. The solvent-free product was a light gray powder with a composition of approximately 15% sterol substituted oligotartrates and the remainder β-sitosterol tartrate dimers.

EXAMPLE 16
β-sitosterol Succinate Carboxy Amide

Initially, the following substances were reacted in nitrogen atmosphere:

10.0 g β-sitosterol hydrogen succinate prepared according to example 3

3.0 ml thionyl chloride 50.0 ml anhydrous cyclohexane

During the reaction, the temperature was kept at approximately 20° C. using a water bath. At first, the mixture was stirred slowly and the β-sitosterol succinate began to dissolve. Simultaneously, $SO_2$ and HCl gases were released from the reaction mixture as bubbles, which left with the $N_2$ stream. The speed of stirring was gradually increased as the sterol succinate dissolution progressed. In other words, the speed of the reaction was kept constant. After the formation of the solution, the temperature was increased very slowly to 40–45° C. and kept constant while stirring vigorously for half an hour, to remove any gaseous substances remaining in the solution.

Next, a 20 $cm^3$ sample was taken with a pipette and transferred to the microdistillation apparatus. The unreacted thionyl chloride was removed from the reaction mixture by distillation in an $N_2$ stream. Distillation was continued until the volume of the remaining liquid was approximately 10 $cm^3$. The concentrated solution was quickly mixed with excess, cold 25% ammonia solution. Fast mixing was continued for half an hour. The surplus ammonia and solvent were evaporated in a vacuum. The precipitate was separated from the water solution by filtration and washed with water, after which the product was dried in a vacuum exsiccator.

The nitrogen content of the product was found to be 1.95%, on the basis of which it was calculated that 72% of the theoretical yield of the desired amide had been obtained.

Using the wave lengths 1660–1680 and $1733 cm^{-1}$, carbonyl absorption in the FTIR spectrophotometer indicated that the product was the desired amide.

EXAMPLE 17
Primary Element Analyses

| Starting materials | % C | % H | | |
|---|---|---|---|---|
| β-sitosterol (technical) | 82.163 | 11.946 | | |
| $C_{29}H_{50}O$ 414.17 g/mol (calculated value) | 83.9 | 12.15 | | |

| β-sitosterol products | composition of primary elements | | | closest molecular |
|---|---|---|---|---|
| | % C | % H | % N | formula |
| Hydrogen succinate (e.g. 3) | 76.59 | 10.63 | | $C_{33}H_{54}O_4$ |
| Citrate (e.g. 4) | 71.57 | 9.38 | | $C_{35}H_{56}O_7$ |
| Citrate dimer | 67.00 | 8.52 | | $C_{41}H_{68}O_{13}$ |
| Diethyl citrate (e.g. 9) | 79.10 | 10.78 | | $C_{66}H_{108}O_7$ |
| Citrate/citr. dimer (e.g. 10) | 68.50 | 9.08 | | |
| Citrate dimer (e.g. 12) | 60.61 | 8.07 | | non-purified raw product |
| Citrate dimer $(NH_4)_2$ (e.g. 13) | 62.05 | 9.04 | 3.63 | $C_{41}H_{68}O_{13}N_2$ |
| Oligo tartrate (e.g. 15) | 53.965 | 7.22 | | —$(C_4H_4O_5)$n-steryl |
| Tartrate dimer | 63.96 | 8.23 | | $C_{37}H_{58}O_{11}$ |

The starting material for the compounds according to the invention was a plant sterol mixture (Weinstein Nutritional Products), composed of 45–55% β-sitosterol, 20–30% campesterol and 15–25% stigmasterol.

EXAMPLE 18
FTIR Spectrums of the Products

The esterification of β-sitosterol (marked *) with various hydroxy acids was determined FTIR spectroscopically.

| | Characteristic absorptions $cm^{-1}$ |
|---|---|
| Example 3* hydrogen succinate | 1178: ester stretching, 1464: CH3 1712: Carboxy carbonyl, 1732: ester carbonyl 2860–3000: sterol C—H, 3440: (wide) H-bonded carboxy-OH (instead OH stretch 1058 is missing from the spectrum). |
| Example 4* citrate deriv. | Strong absorption from the ester at 1194–1197; 1463: CH3, strong band of fusion 1733–1737 suits ester carbonyl, absorption model (typical) for C—H hydrogen sterol ring system visible 2860–3000; Area 3000–3500 wide, absorption band - most likely citrate-OH and carboxyl-OH groups: can sometimes distinguish absorption 3450 (wide). |
| Example 9 di-*ethyl citrate | Absorption from ester at 1193–1199 and 1219–1222, 1463: CH3, 2 strong ester carbonyl bands 1725–1733 and 1776, a characteristic C—H absorption band for sterols 2860–3000; hydrogen-bonded OH absorption 3431. |
| Example 13 *citrate dimer $(NH_2)_4$ | 1725: ester carbonyl, 2859: sterol C—H, 2945: sterol C—H, 3224 and 3403 wide bands. |
| Example 15 *tartrate oligomers | 1084 suitable for OH stretch, 1203–1225 wide absorption band most likely related to ester bond, absorption 1442; 1464 suitable for the methyl groups of the sterol structure; strong absorption in the carbonyl area 1743; very wide, strong |

| | Characteristic absorptions cm$^{-1}$ |
|---|---|
| | absorption 2500–3500; concentrated at 3433, originates from hydrogen-bonded OH and carboxyl groups. In the range 2869–3000 partially covered CH absorption whose model [2869, 2936] also indicates that this is a substituted sterol in question. |
| | References |
| Technical β-sitosterol | 1058: OH stretch, 1464 CH3: 2860–3000 [2868, 2937 more characteristic] Sterol C—H, 3390: hydrogen-bonded OH. |
| β-sitosterol acetate | 1058 cm$^{-1}$    OH stretch; missing |
| | 1731              ester carbonyl |
| | 2668, 2937        sterol C—H |
| | 3390              hydrogen-bonded OH; missing |
| Acetyl triethyl citrate | 1736 cm$^{-1}$    ester carbonyls, strong |
| | 2981              medium, C—H |

EXAMPLE 19

β-sitosterol Lactate

The following substances were allowed to react in toluene solution:

25.0 g β-sitosterol 30.0 g 90% (S)-2-hydroxy propionic acid (L-lactic acid) water solution 100.0 ml toluene A minimum of 7 ml of water was azeotropically distilled from the reaction mixture over 7–8 hours; as the conversion approached theoretical, upon cooling no lactic acid or plant sterols were crystallized from the reaction mixture. The cooled reaction mixture was a yellowish, viscose liquid. The toluene was removed from the reaction mixture in a vacuum (29 mmHg) at a temperature of 80–90° C. At a temperature of 60–100° C., the reaction product was a light-colored, yellowish, viscose liquid that was soluble in lipids and ethanol. As a whole, the material obtained was useable and contained very little or no free plant sterols and/or lactic acid.

EXAMPLE 20

β-sitosterol Lactate

Preparation with Fischer Apparatus 200 g β-sitosterol, 250 g lactic acid, and 500 ml toluene were dissolved in a 5 l flask. The mixture was refluxed at 110–115° C. at the same time as water (free water+reaction water) was collected using water separation apparatus, in order to monitor the progress of the reaction. Reaction time was 11.5 h. At this point, 68 ml of water had been collected (free water: 33.8 ml+reaction water 34.2 ml), representing a 77.5% conversion in relation to the starting material. The toluene was evaporated from the reaction mixture using a rotavapor, and the product was dried in a vacuum oven at 40–60° C. The esterification experiment was repeated 5 times.

EXAMPLE 21

β-sitostanol Derivatives

Stanol Lactate

The stanol lactate was produced using the same method as the β-sitosterol lactate except that the starting material was β-sitostanol

EXAMPLE 22

β-sitostanol Derivatives

Stanol Lactate; the Hydrogenation of Sterol Lactate 0.2 kg β-sitosterol lactate was dissolved in 5 kg ethanol (96.4 volume-%, Primalco Oy, Nurmijärvi) and the same hydrogenation process was carried out as in the production of β-sitostanol. A filter was used to separate the hydrogenation catalyst from the reaction mixture. The ethanol solution was concentrated by evaporation and the separated raw material was decanted. The raw product was again dissolved into a 10% solution of ethanol and precipitated by adding excess water. The precipitate could be filtered when the water—ethanol ratio was 1:2. The resulting product was air-dried and then vacuum-dried at 20° C.

EXAMPLE 23

The production of β-sitosterol Dicarboxylic Acid Derivatives

β-sitosterol Succinate Glycerol Ester

The β-sitosterol hemisuccinate was reacted with glycerol while toluene was used as an azeotrope forming agent, as in example 19.

Ethyl β-sitosteryl Succinate

By transesterification at 180–200° C. in the presence of a H+ catalyst, the β-sitosterol and the diethyl succinate are in a molar ratio of 1:2. The excess of diethyl succinate was distilled at 100–150° C. and 0.3 mmHg.

EXAMPLE 24

The β-sitosterol succinyl chloride was reacted with triethyl citrate in toluene with a molar ratio of 1:1. The acting HCl acceptor in the reaction mixture is pyridine (1 mol pyridine per 1 mol β-sitosterol succinate chloride).

EXAMPLE 25

Acetic Acid Dispersions 6.80 g β-sitosterol citrate from example 12 90.7 g Rajamäki Spirit Vinegar (Primalco Oy, Nurmijärvi), containing 10 weight-% acetic acid.

The mixture was allowed to stand without stirring for 12 hours. Determination of the amount of soluble matter from the solution showed that 0.74% of the sterol citrate had dissolved. The mixture was stirred for 6 hours, after which it was stirred rapidly with an Ultra Turrax homogenizer for at least 2 min.

The concentration of the final dispersion was found to be 7 weight-%. The dispersion was stable for at least three days, the cup viscosity was 30 s and the Brookfield viscosity η 124 cp at 23° C.

EXAMPLE 26

35.0 g β-sitosterol citrate acetic acid dispersion from example 31 and 60.0 g cooking oil (5 weight-% β-sitostanol lactate, 0.5 g salt, 11.5 g sugar and 3.0 g spices, white pepper, ground garlic or mustard) were measured. The mixture contained 7.45 weight-% sterol derivative and had 55 weight-% fat content.

It was noted that a salad dressing containing acetic acid could be produced from the compounds in question, whose plant sterol or stanol content is comparable to a common plant stanol containing margarine.

EXAMPLE 27

Light Spreads Containing Phytosterol

The products are made according to the following recipe. Initially, the following components were combined:

100 g cooking oil 100 g margarine

The margarine was allowed to soften at room temperature.

100 g water 250 g cottage cheese 2 tsp. spice mix (parsley/chives)
were added

The phytosterol esters were added to the product dissolved in cooking oil; the reference-sample is according to the basic recipe.

| β-sitosterol ester (*) | % total fat | Result |
| --- | --- | --- |
| Spread No. 1 (*) hemisuccinate | 5,0 | excellent tructure withstands mixing |
| Spread No. 2 (*) citrate | 2,5 | good/better than reference-sample |
| Spread No. 3 (*) lactate | 5,0 | good/spreadable |

EXAMPLE 28
Various Types of Mayonnaise Containing β-sitosterol

Products were made in a food processor according to the following recipe:
 1 egg
 2 tsp. mustard
 1 tsp. salt
Homogenize at full speed for 60 s
 Add 1 tbsp. Rajamäki Honey-Cider Vinegar (Primalco Oy, Nurmijärvi)
Homogenize at full speed for 15 s
 Add 2 dl dietary oil while mixing at full speed The β-sitosterol esters were added to the products while dissolved in dietary oil. The reference-sample was a product made according to the basic recipe. The mixing times for all samples were exactly the same.

| Mayonnaise | β-sitosterol derivative | % fat | salt added/not added |
| --- | --- | --- | --- |
| No. 1 | * hemisuccinate | 2,5 | same as reference - sample |
| No. 2 | * hemisuccinate | 2,5 | not added |
| No. 3 | * citrate | 2,5 | not added |

Evaluation of results:

No. 1 more viscous than reference-sample; stronger flavor, but not unpleasant

No. 2 same viscosity as previous; no complaints about taste

No. 3 excellent structure, very dense, stays intact, no complaints about taste.

EXAMPLE 29
Chocolate-flavored Mint Truffle Containing β-sitosterol
 250 g plain chocolate
 2,0 g β-sitosterol hemisuccinate
 1 dl cream
 1 egg yolk
 3 tbsp. butter
 2 drops mint oil The chocolate was melted in a water bath and the β-sitosterol hemisuccinate was added and allowed to dissolve while being stirred intermittently; after which the mixture was allowed to stand. The cream and butter were heated to boiling point while being stirred constantly; the heating was interrupted and the egg yolk added. The mixture was re-heated while being vigorously mixed until it began to thicken, after which the heating was stopped.

After this, the chocolate was gradually added to the mixture, then allowed to cool a little and then the mint oil drops were added. Lumps were lifted out of the mixture and allowed to cool in a cold place. The truffles obtained had a homogenous composition, an even cut surface and an excellent taste.

EXAMPLE 30

2.0 g of β-sitosterol hemisuccinate were dissolved in 125 g of coconut fat in a water bath. 1 dl of icing sugar were whipped stiffly with one egg yolk. ½ dl of cocoa powder was then added and mixed well.

The coconut fat containing the β-sitosterol hemisuccinate was added to the cooled mixture, while stirring constantly, and mixing was continued until the mixture thickened to the point that candies could be formed from it. The truffles obtained were kept in a refrigerator.

If the truffles made in this way are compared with truffles made in the same way, but without the β-sitosterol hemisuccinate, it will be noted that there is no difference in the taste of the products. The truffles have a shiny outer surface and a homogenous composition.

EXAMPLE 31
A Cream Liqueur Containing β-sitosterol 2,0 g β-sitosterol hemisuccinate was dissolved into 550 g cream liquor concentrate (Creamy Creation, DMV, Division of Campina, Melkunie, the Netherlands) containing 12% fat, while mixing at 40–65° C., so that thus the product's fatty portion contains 3% β-sitosterol ester.

115 ml 96.4% alcohol was added and mixed well. 160 g starch fluid sugar FFS (Neson, Finland), with a 70% dry matter content, was added and mixed. Finally, 250 ml water was added, stirring continuously. If desired, chocolate aroma, for example, can be added to the beverage.

This yields a cream liqueur with an alcohol content of 18 vol.-%.

What is claimed is:

1. A phytostanol poly(hydroxy alkanoate), poly(L-lactic acid), or amino acid ester, salts of said acids, mixed esters of dicarboxylic acids with polyols or polyol ($C_2$–$C_{22}$) fatty acid esters, mixed esters of hydroxy acids with alcohols or polyols or polyol ($C_2$–$C_{22}$) fatty acid esters or ($C_2$–$C_{22}$) fatty acid esters of said hydroxy acids.

2. A phytostanol according to claim 1, wherein the phytostanol is a β-sitostanol.

3. An ester according to claim 1 or 2, wherein said ester is hydrophilic and soluble in fat.

4. An ester according to claim 1, wherein said ester is hydrophilic, fat-soluble and soluble in fat emulsions.

5. A phytostanol dicarboxylic acid hemiester, hydroxy acid, oligo- or polyester, or α-amino acid ester.

6. A phytostanol ester formed with succinic acid, glutaric acid, ketoglutaric acid, tartaric acid, malic acid, citric acid, lactic acid or 3(R)-hydroxy-butyric acid, a phytostanol ester formed with an amino acid derivable from a protein, or a phytostanol ester formed with a derivative of these acids.

7. A dicarboxylic acid derivative of a phytostanol with the formula $$S\text{—}O_2CRCO_2Y \qquad (I)$$

S=phytostanol
R=$C_2$–$C_6$ carbon chain
Y=H or —$C_2H_5$ or formula I, in which $$Y = \underset{(2S)}{-\overset{*}{C}H(CH_3)(CO_2Y_1)} \quad (II)$$

$Y_1$=H or $C_2H_5$
or formula I, in which $$Y = -\underset{R_1}{\overset{(*)}{C}}HCH_2CO_2Y_2 \quad (III)$$

$Y_2$=H or $C_2H_5$ and
$R_1$=$C_2$–$C_6$ alkyl
or a formula I, in which $$Y = -\underset{CH_3}{\overset{(*)\,(3R)}{C}}HCH_2CO_2Y_3 \quad (IV)$$

$Y_3$=H or $C_2H_5$.

8. An amino acid derivative of a phytosterol or phytostanol, with the formula:

$$S-O_2\overset{\uparrow}{\underset{NH_2}{C}}HR \quad (V)$$

S=phytosterol or phytostanol
R=H or the structure appearing in natural L-amino acids.

9. A citric acid derivative of a phytosterol or phytostanol, with the formula $$S-O_2CCH_2\underset{CO_2R_2}{\overset{OR_3}{C}}CH_2CO_2R_1 \quad (VI)$$

S=phytosterol or phytostanol;
$R_1$=$R_2$=H and $R_3$=$C_2$–$C_{22}$ carboxyl acid residue
or
$R_1$=$R_2$=—$C_2H_5$ and $R_3$=H
or
$R_1$=$R_2$=—$C_2H_5$ and $R_3$=$C_2$–$C_{22}$ carboxyl acid residue
or
$R_1$=$R_2$=—$CH_2CHOHCH_2OH$ and $R_3$=H
or
$R_1$=$R_2$=—$CH_2CHOHCH_2OH$ and $R_3$=$OCCH_3$.

10. A tartaric acid derivative of a phytosterol or a phytostanol, with the formula:

$$S-O_2CCH(OR_1)CH(OR_2)CO_2Y \quad (VII)$$

S=phytosterol and/or phytostanol
$R_1$=$R_2$=H and Y=$C_2H_5$
or
$R_1$=$R_2$=acyl $C_2$–$C_{22}$ and Y=H
or
$R_1$=$R_2$=acyl $C_2$–$C_{22}$ and Y=$C_2H_5$.

11. A 3(R)-hydroxy butyric acid ester of phytosterol and/or phytostanol or its derivative or salt.

12. A method of preparing phytostanol derivatives comprising:
preparing a phytosterol ester by esterification of a phytosterol with phytosterol hydroxy acid, keto acid, dicarboxylic acid or amino acid ester;
hydrogenating said phytosterol ester in a concentrated ethanol or acetic acid solution to form a hydrogenation solution containing phytostanol derivatives.

13. A method according to claim 12, wherein the phytosterol ester is prepared with succinic acid, maleic acid, glutaric acid, keto glutaric acid, tartaric acid, malic acid, citric acid, lactic acid, 3(R)-hydroxy butyric acid or an amino acid derivable from proteins.

14. A method of preparing alcoholic beverages or vinegar products, which comprises adding the hydrogenation solution according to claim 12 or 13 to an alcoholic beverage or a vinegar product.

15. A dietary fat composition comprising:
one or more of compounds selected from the group consisting of a phytosterol hydroxy acid or amino acid ester, a salt of said acids, a mixed ester of dicarboxylic acids with alcohols, polyols or polyol ($C_2$–$C_{22}$)fatty acid esters, a mixed ester of said hydroxy acids with alcohols, polyols or polyol ($C_2$–$C_{22}$)fatty acid esters, and a ($C_2$–$C_{22}$)fatty acid ester of said hydroxy acids; and
dietary fat.

16. A dietary fat composition comprising:
one or more of compounds selected from the group consisting of a phytostanol hydroxy acid, dicarboxylic acid or amino acid ester, a salt of said acids, a mixed ester of said dicarboxylic acids with alcohols, polyols or polyol ($C_2$–$C_{22}$)fatty acid esters, a mixed ester of said hydroxy acids with alcohols, polyols or polyol ($C_2$–$C_{22}$)fatty acid esters, and a ($C_2$–$C_{22}$)fatty acid ester of said hydroxy acids; and
dietary fat.

17. A dietary fat composition comprising:
one or more of compounds selected from the group consisting of a β-sitosterol and/or β-sitostanol dicarboxylic acid hemiester, hydroxy acid ester, oligo- or polyester, hydroxy acid mixed ester, dicarboxylic acid mixed ester, and α-amino acid ester; and
dietary fat.

18. A dietary fat composition comprising:
one or more of compounds selected from the group consisting of a phytosterol and/or phytostanol ester formed with succinic acid, glutaric acid, malic acid, tartaric acid, citric acid, lactic acid or 3(R)-hydroxybutyric acid, phytosterol and/or phytostanol ester with an amino acid derivable from a protein, and phytosterol and/or phytostanol ester formed with a derivative of these acids; and
dietary fat.

19. A composition according to claim 15 or 16, wherein the fatty component of the composition contains 0.1–10 weight-% of the compounds.

20. A food product, comprising:
any one of the dietary fat compositions of claim 15, 16, 17, or 18; and
a food ingredient.

21. A food product according to claim 20, wherein it is a margarine, light spread or mayonnaise.

22. A food product according to claim 20, wherein it is a mustard.

23. A food product according to claim 20, wherein it is a product containing milk fat.

24. A food product according to claim 20, wherein it is a plant oil product intended for dietary use.

25. A food product according to claim 20, wherein it is a dietary oil.

26. A food product according to claim 20, wherein it is an alcoholic beverage with a fat content.

27. A food product according to claim 20, further comprising water and/or an acetic acid component, wherein said one or more compounds are dissolved and/or dispersed in both the fat and the water and/or acetic acid components of the food product.

28. A food product according to claim 20, further comprising a component with an alcohol content wherein said one or more compounds are dissolved and/or dispersed in both the fat and the water and/or ethanol components of the food product.

29. A composition according to claim 19, wherein the fatty component of the composition contains 1–10 weight-% of the compounds.

* * * * *